(12) United States Patent
Jeannotte (10) Patent No.: US 10,151,686 B2
(45) Date of Patent: Dec. 11, 2018

(54) FLOW CELLS FOR DIFFERENTIAL REFRACTIVE INDEX DETECTION

(75) Inventor: Anthony C. Jeannotte, Foxborough, MA (US)

(73) Assignee: WATERS TECHNOLOGIES CORPORATION, Milford, MA (US)

(*) Notice: Subject to any disclaimer, the term of this patent is extended or adjusted under 35 U.S.C. 154(b) by 0 days.

(21) Appl. No.: 14/238,045

(22) PCT Filed: Aug. 16, 2012

(86) PCT No.: PCT/US2012/051028
§ 371 (c)(1),
(2), (4) Date: Feb. 10, 2014

(87) PCT Pub. No.: WO2013/025851
PCT Pub. Date: Feb. 21, 2013

(65) Prior Publication Data
US 2014/0192350 A1    Jul. 10, 2014

Related U.S. Application Data

(60) Provisional application No. 61/523,915, filed on Aug. 16, 2011.

(51) Int. Cl.
*G01N 21/05* (2006.01)
*G01N 21/03* (2006.01)
*G01N 21/41* (2006.01)

(52) U.S. Cl.
CPC ......... *G01N 21/05* (2013.01); *G01N 21/0303* (2013.01); *G01N 21/4133* (2013.01);
(Continued)

(58) Field of Classification Search
CPC ... G01N 2021/0346; G01N 2021/0389; G01N 2021/4146; G01N 2021/414;
(Continued)

(56) References Cited

U.S. PATENT DOCUMENTS 3,612,697 A    10/1971  Nebe et al.
3,983,390 A *   9/1976  Llop ............... G01N 21/4133
                                                   250/231.1
(Continued)

FOREIGN PATENT DOCUMENTS

CN    1648639 B    9/2010
EP    0 504 797 A2  9/1992
(Continued)

OTHER PUBLICATIONS

International Search Report and Written Opinion for PCT/US2012/051028, dated Oct. 26, 2012, pp. 9.
(Continued)

*Primary Examiner* — Gordon J Stock, Jr.
(74) *Attorney, Agent, or Firm* — Schmeiser, Olsen & Watts LLP (57) ABSTRACT

A flow cell for differential refractive index detection. The flow cell includes a transparent body that extends from a first end to a second end along a longitudinal axis. The transparent body defines a sample prism chamber and reference prism chamber. The sample prism chamber is configured to allow fluid flow between the first and second ends of the transparent body along the longitudinal axis. The reference prism chamber is configured to receive a reference fluid. The sample and reference prism chambers each include a grating comprising a plurality of grooves extending along the longitudinal axis in the direction of fluid flow.

30 Claims, 6 Drawing Sheets

(52) U.S. Cl.
CPC ........... *G01N 2021/0346* (2013.01); *G01N 2021/0389* (2013.01); *G01N 2021/4146* (2013.01); *G01N 2021/4153* (2013.01)

(58) Field of Classification Search
CPC ........... G01N 2021/4153; G01N 21/05; G01N 21/07; G01N 21/09; G01N 21/0303; G01N 21/4133
See application file for complete search history.

(56) References Cited

U.S. PATENT DOCUMENTS

| | | | | |
|---|---|---|---|---|
| 4,436,420 | A | * 3/1984 | Depp | G01N 21/4133 356/128 |
| 5,319,399 | A | 6/1994 | Hudgins | |
| 5,347,358 | A | 9/1994 | Nebe et al. | |
| 2009/0079976 | A1 * | 3/2009 | Cunningham | B01L 3/5027 356/246 |
| 2009/0103076 | A1 * | 4/2009 | Gloeckner | G01N 21/4133 356/137 |
| 2009/0278447 | A1 | 11/2009 | Saitoh et al. | |
| 2010/0231911 | A1 | 9/2010 | Fischer et al. | |
| 2014/0080729 | A1 * | 3/2014 | Grego | G01N 21/05 506/9 |

FOREIGN PATENT DOCUMENTS

| | | | |
|---|---|---|---|
| EP | 1 560 016 | A1 | 8/2005 |
| GB | 1508783 | A * | 4/1978 |
| JP | 63-132139 | A | 6/1988 |
| JP | 07-286957 | A | 10/1995 |
| JP | 2001-501299 | A | 1/2001 |
| JP | 2003-121350 | A | 4/2003 |
| JP | 2005-214967 | A | 8/2005 |
| JP | 2008-297535 | A | 12/2008 |
| WO | 2007/000187 | A1 | 1/2007 |

OTHER PUBLICATIONS

Chinese Office Action for Application No. 201280039750.9, dated May 21, 2015 (23 pages).
Extended European Search Report for Application No. 12823817.7, dated Feb. 17, 2015 (6 pages).
Japanese Search Report for Application No. 2014-526190, dated Jul. 27, 2016 (69 pages).
Japanese Office Action for Application No. 2014-526190, dated Aug. 2, 2016 (7 pages).
International Preliminary Report on Patentability in International Patent Application No. PCT/US2012/051028, dated Feb. 27, 2014; 7 pages.

* cited by examiner

FLOW CELLS FOR DIFFERENTIAL REFRACTIVE INDEX DETECTION

CROSS REFERENCE TO RELATED APPLICATION

This application is the National Stage of International Application No. PCT/US2012/051028, filed on Aug. 16, 2012, which claims priority to and benefit of U.S. Provisional Application No. 61/523,915, filed Aug. 16, 2011. The contents and teachings of each of these applications are hereby expressly incorporated herein by reference in their entirety.

TECHNICAL FIELD

This disclosure relates to flow cells for differential refractive index detection.

BACKGROUND

The principles of differential refractive index (RI) detection are generally well-known. Differential refractive detectors examine the difference in refractive index of a fluid stream (the "sample" path containing one or more analytes to be detected contained within a mobile phase) with that of an analyte-free, often static, fluid sample, namely the "reference." Various optical methods such as beam deflection, Fresnel reflection or interferometry have been employed to accomplish this measurement. Refractive index detectors are frequently employed for analysis in liquid chromatography, particularly when the analyte(s) of interest lack a suitable UV chromophore.

The refractive index of analyte-bearing solutions is substantially linearly dependent upon analyte concentration. The index difference between the sample and reference fluids often spans a concentration range of nearly $10^7$. Corresponding refractive index differences ranges from $10^{-9}$ to $10^{-2}$ RI units. For example, water has a refractive index in the visible region of the spectrum of approximately 1.333; a high-end analyte concentration could increase this value to 1.3335 the difference equaling 0.0005 RI units (or 0.5 milliRI units where 1 milliRI=0.001 RI units). Depending upon the analyte and mobile phase the index difference may be positive or negative. A frequently employed optical method is the so-called beam deflection method whereby an optical beam ("light ray") is directed through a flow cell containing side-by-side prismatic-shaped chambers: the sample fluid flows along the long axis of the chamber—that is—in a direction normal to a plane containing the prismatic or triangular profile. One chamber contains the sample under test while the second contains the reference fluid. The light rays (optical beams) passing through each chamber are refracted to a degree which depends upon the absolute index within each chamber and, upon emerging from the cell will have an overall deflection angle which is relatable to the index difference between the fluids within the chambers. This deflection angle leads to a change in the position of the optical beam at a plane of detection at which is located light detection means such as one or more photodiodes. Thus, in the case of two photodiodes, when there is no refractive index difference each detector reports a substantially equal signal level associated with this balanced condition. If an analyte alters the refractive index of the sample (prism) chamber, one of the detector signals increases while the other decreases since the beam has now been deflected from its initial position. These two signals are processed in such a way as to yield a value for the refractive index difference and, through a calibration step which would precede this experiment, output a reading for the analyte concentration.

A limitation of the conventional prismatic (often a right triangle) shaped chamber is the dispersive character of its geometry. Unlike a circular fluid conduit, the fluid velocity profiles in a triangular shaped conduit are very asymmetric which tends to increase the dispersion or peak width of a chromatographic peak which has eluted from the column. Despite these limitations, a differential RI detector is viewed as an important tool in the arsenal of the chromatographer since it enables the detection of analytes which lack a suitable chromophore for detection by typically more sensitive methods such as UV absorbance or fluorescence. While these limitations are manageable when the incoming chromatographic peak itself is relatively broad, such as might be produced from chromatographic columns with internal diameters in the range of 4.8-7.6 mm and larger, the trend towards smaller column diameters for greater separation efficiencies and reduced solvent consumption means greater attention must be focused on minimizing post-column dispersion, including the contribution from the flow cell itself.

SUMMARY

The invention arises, in part, from the realization that a flow cell for refractive index detection can be provided with a geometry that can contribute to improved fluid velocity profiles and which can also offer an overall lower volume as compared to conventional flow cells. In particular, prism chambers of a flow cell can be provided with gratings which can help to reduce the fluid volumes of the prism chambers while not significantly detracting from overall performance of the flow cell.

Accordingly, one aspect of the invention features a flow cell for differential refractive index detection. The flow cell includes a transparent body that extends from a first end to a second end along a longitudinal axis. The transparent body defines a sample prism chamber and reference prism chamber. The sample prism chamber is configured to allow fluid flow between the first and second ends of the transparent body along the longitudinal axis. The reference prism chamber is configured to receive a reference fluid. The sample and reference prism chambers each include a grating comprising a plurality of grooves extending along the longitudinal axis in the direction of fluid flow.

Another aspect of the invention features a flow cell for differential refractive index detection. The flow cell includes a transparent body that extends from a first end to a second end along a longitudinal axis. The transparent body includes a first prism chamber and a second prism chamber. The first prism chamber is configured to allow fluid flow between the first and second ends of the transparent body along the longitudinal axis. The first prism chamber includes a grating comprising a plurality of grooves extending along the longitudinal axis in the direction of fluid flow.

In yet another aspect, the invention features a method that includes directing an optical beam through a flow cell containing sample and reference prism chamber, conveying a fluid flow through the sample prism chamber; and detecting presence of an analyte in the fluid flow based on a detected deflection of the optical beam. The sample prism chamber includes a grating comprising a plurality of grooves extending parallel to the direction of the fluid flow.

In a further aspect, the invention features a method that includes molding an optical grade transparent polymer to form a transparent body for a flow cell. The transparent body defines a sample prism chamber configured to allow fluid flow through the transparent body and comprising a grating and a reference prism chamber configured to receive a reference fluid. The method also includes depositing a protective surface layer on surfaces of the transparent body to make the sample and reference chambers resistant to fluids that are to be contained within these chambers. In some cases the fluid to be contained may be, for example, a liquid chromatography mobile phase.

Implementations can provide one or more of the following advantages.

In some implementations, a flow cell geometry is provided that helps to achieve improved fluid velocity profiles and that can also enable an overall lower volume cell.

In some cases, a flow cell geometry is provided that is beneficial to minimize analyte peak broadening or peak dispersion.

In some implementations, methods of construction of flow cells for refractive index detection are provided which can help to improve its manufacturing yield at an overall lower cost.

Other aspects, features, and advantages are in the description, drawings, and claims.

BRIEF DESCRIPTION OF THE DRAWINGS

Like reference numbers indicate like elements.

DETAILED DESCRIPTION

Figure 1:
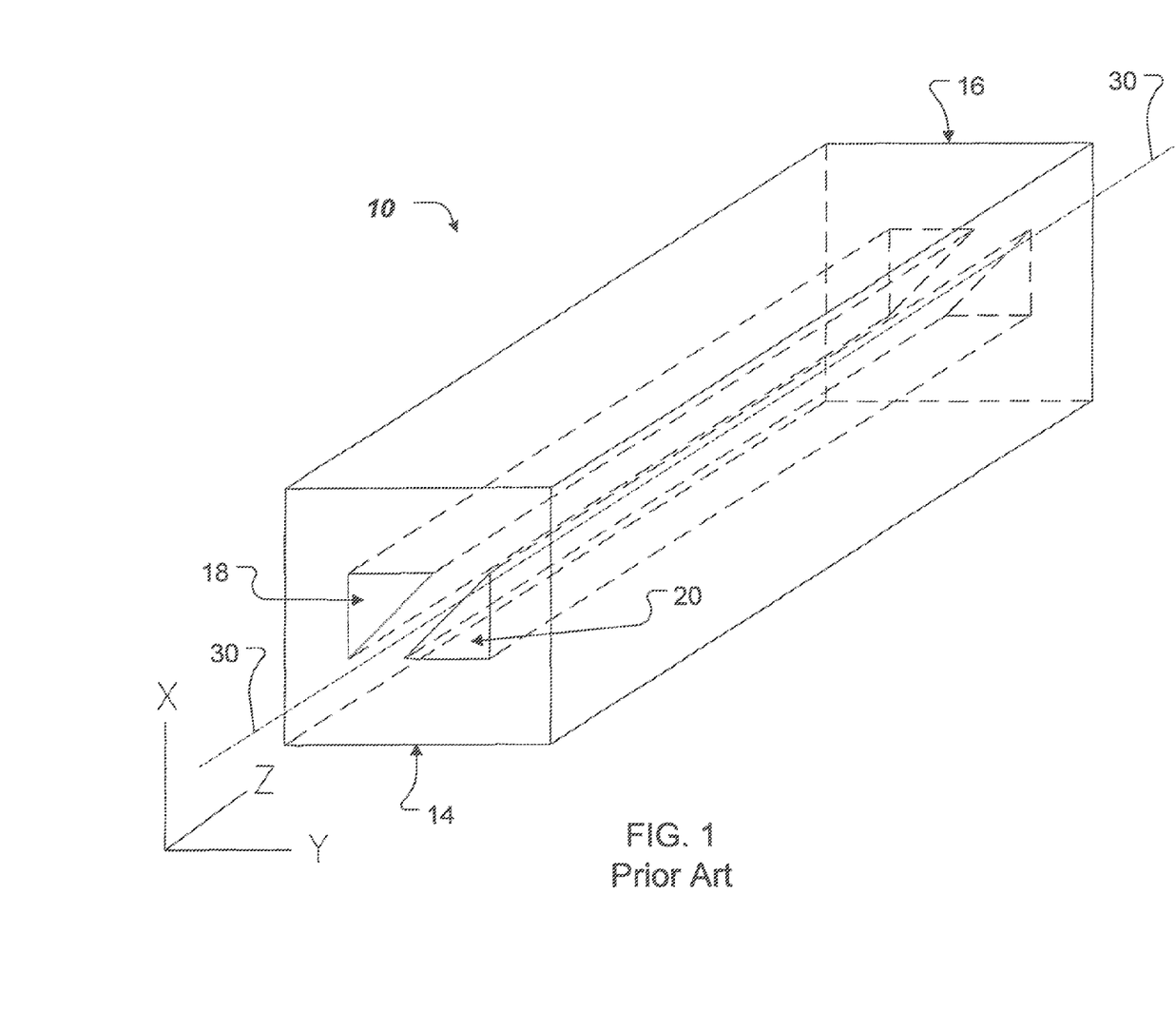
FIG. 1 is a perspective view of a transparent body of a conventional flow cell for differential refractive index detection.
Figure 2:
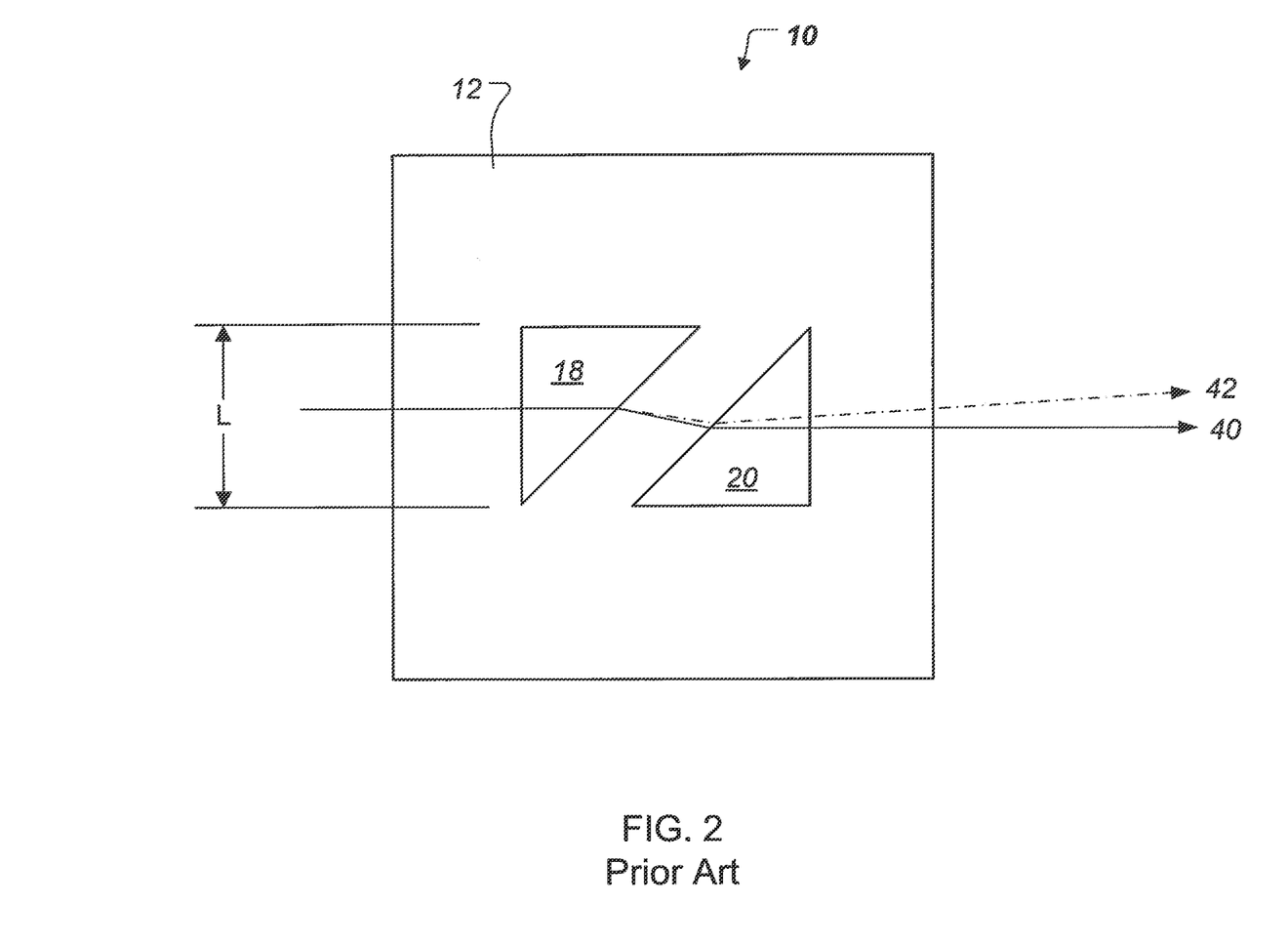
FIG. 2 is a cross-sectional view of the transparent body of FIG. 1 showing a light ray passing through the transparent body.

A conventional prismatic chambered flow cell 10 employed for differential RI detection via beam deflection is shown in FIGS. 1 and 2. Such conventional flow cells are commercially available from NSG Precision Cells. Referring to FIG. 1, the conventional flow cell 10 includes a transparent body 12 having a pair of prism chambers, which extend between first and second ends 14, 16 of the transparent body 12. The prism chambers include a sample prism chamber 18, for receiving a flow of sample fluid, and a reference prism chamber 20 for receiving a reference fluid. The order of the chambers may be reversed; that is, the body 12 may be rotated by 180° about the X or Z axis without altering the essential features of the beam deflection process. Cell end caps or fluid inlet and exit ports (not shown), for conveying fluid into and out of the prism chambers 18, 20, are typically located near the ends 14, 16 of the transparent body 12. The fluid ports may lie in either the X-Y or Y-Z plane but more typically they are perpendicular to the longitudinal axis 30 of the conventional flow cell 10, shown in FIG. 1 as parallel to the Z-axis. The actual size of the prism chambers 18, 20 is usually dictated by manufacturing and functional requirements such as peak volumes, optical detection sensitivity and other variables of concern to the instrument designer.

FIG. 2 shows a cross-section view through the conventional flow cell 10 in which a single ray 40 is shown passing through the two prism chambers 18, 20. In a balance condition, the refractive indices of fluids in the sample and reference prism chambers 18, 20 are the same and the ray 40 passes through the conventional flow cell 10 without a change in its inclination angle. A second ray 42 corresponds to a condition in which the refractive index of a fluid (a sample fluid) in the sample prism chamber 18 differs from the refractive index of a fluid (a reference fluid) in the reference prism chamber 20, leading to a net deflection of the incident ray which deflection is measurable based on a change in signals sensed by one or more detectors.

Optical systems can be employed to collect and direct light from a light source through the conventional flow cell 10 then collect light which has passed through the conventional flow cell 10 and direct it to one or more light detectors (e.g., photodiodes). Continuous readings from the light detector(s) while a stream of the sample fluid, e.g., flowing from the outlet of an upstream chromatography column, enters and passes through the sample prism chamber 18 are monitored to identify both the time and amplitude of analyte peaks that have been produced by upstream chromatographic separation. An analyte peak entering the conventional flow cell 10 will be characterized as having a certain width, indicative of the efficiency with which it was separated by the column. This peak will typically broaden as it passes through the conventional flow cell 10 and it is one object of flow cell design to minimize this broadening or peak dispersion. Other things being equal, a triangular-shaped flow conduit can be expected to result in greater dispersion than a circular shape. Abrupt changes in the cross-section of a conduit can result in disturbances to the flow profile and that these disturbances can give rise to regions of low or stagnant flow, or otherwise poorly-swept regions which increase peak dispersion and reduce detection sensitivity since the analyte is now distributed over a larger fluid volume which decreases its concentration.

Figure 3A:
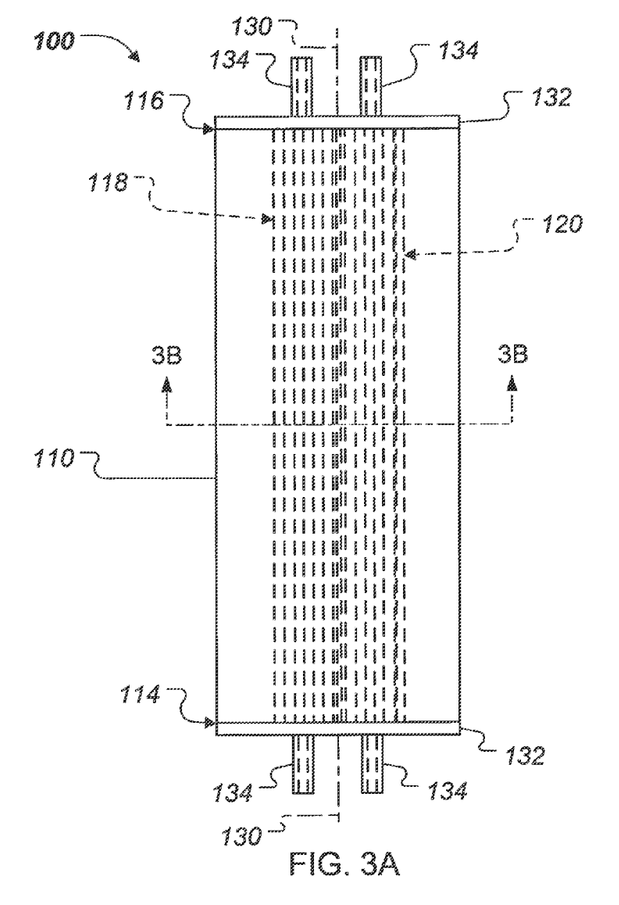
FIG. 3A is a top plan view of a transparent body of an echelle flow cell for differential refractive index detection.
Figure 3B:
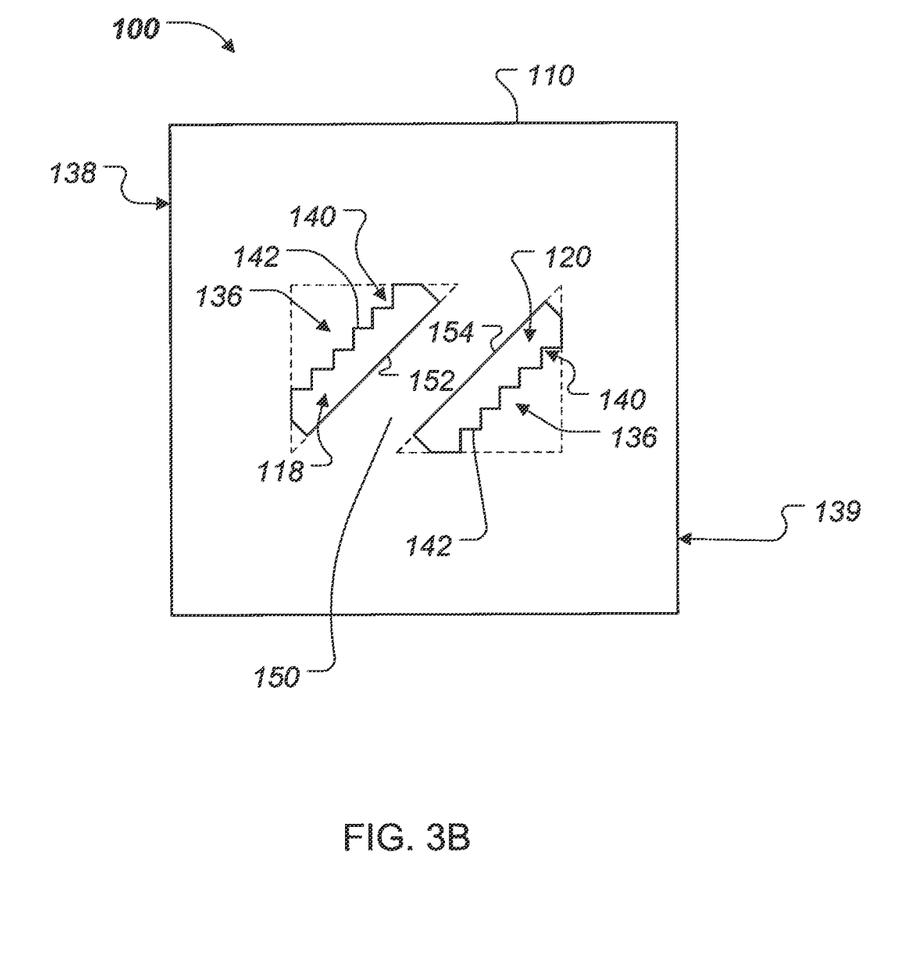
FIG. 3B is a cross-sectional view of the transparent body of FIG. 3A taken along line 3B-3B.

FIGS. 3A and 3B illustrate an implementation of a flow cell 100 for RI detection in accordance with the present invention. The flow cell 100 performs essentially the same function as the conventional flow cell 10 of FIG. 1; however, it differs from the conventional flow cell in that it has an alternative geometry which can contribute to improved fluid velocity profiles and can provide an overall lower volume cell.

The flow cell 100 includes a transparent body 110 that extends from a first end 114 to a second end 116 along a longitudinal axis 130. The transparent body 110 defines a pair of prism chambers including a sample prism chamber 118 and a reference prism chamber 120. The flow cell 100 also includes an end cap 132 at each end 114, 116 of the transparent body 110. Each of the cell end caps 132 includes fluid ports 134 in fluid communication with the prism chambers 118, 120 for conveying fluid into and out of the prism chambers 118, 120.

Notably, the prism chambers 118, 120 each include a grating 136. The gratings 136 are arranged at an angle of about 5 degrees to about 85 degrees, e.g., 45 degrees, relative to first and second outer optical surfaces 138, 139 of the transparent body 110. The grating is an array of parallel spaced grooves 140. The grooves 140 extend along the longitudinal axis 130 of the transparent body 110 in the direction of (parallel to) fluid flow (the direction that fluid moves through the sample prism chamber). Arrangements in which grooves or steps are perpendicular to the direction of fluid flow can contribute to the formation of eddies (i.e., localized areas of turbulence) which can potentially lead to unwanted mixing of fluid species and may contribute to analyte peak broadening or peak dispersion.

These gratings 136 allow the prism chambers 118, 120 to have smaller volume than the corresponding 'triangle' chambers depicted in FIG. 2 (and shown in FIG. 3B as dashed lines). The gratings 136 can be an echelle grating as illustrated in FIGS. 3A and 3B. An echelle grating is typically a type of grating which has a low groove density (e.g., grooves per millimeter). Except for corners at the acute angles of the triangle, the echelle grating preserves the same optical edge length ("L" in FIG. 2) as the full triangle, thus preserving the same frontal area, but with an overall lower cross-sectional area (and thus volume when consideration is given to the Z-length of the chamber). This is illustrated in FIG. 3B which depicts the outline of the triangular cross-section in dashed lines. As a result of these geometrical differences, the cross-sectional area of the flow cell 100 is smaller than that of the conventional cell 10, thereby providing a flow cell 100 having a volume, for example, that is 4× smaller. Increasing the groove density can allow for further reductions in volume.

Figure 3C:
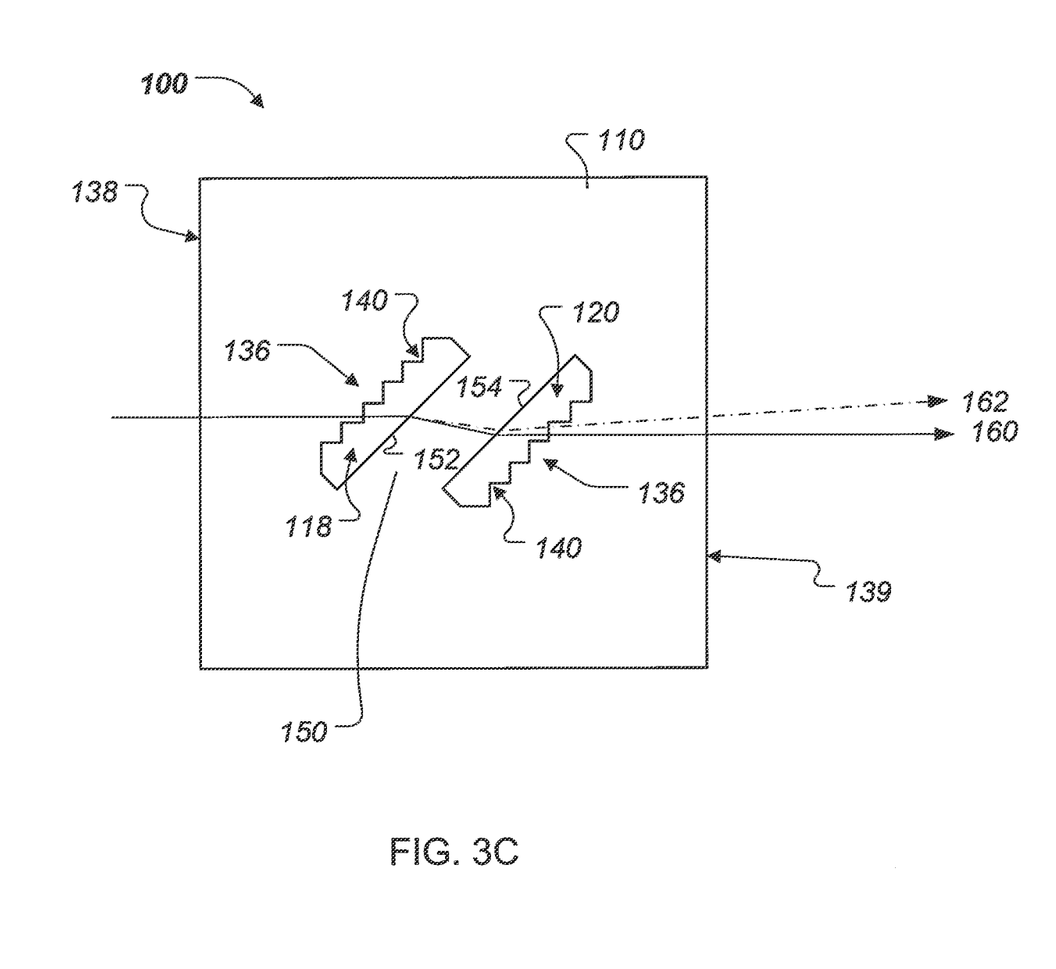
FIG. 3C is a cross-sectional view of the transparent body of FIG. 3A showing a light ray passing through the transparent body.

The sample and reference prism chambers 118, 120 are separated by a transparent partition wall 150 having first and second, opposing smooth surfaces 152, 154 defining at least one boundary of each prism chamber 118, 120. The transparent partition wall 150 may be an integral part of the transparent body 110 and is arranged parallel to the gratings and at an angle of about 5 degrees to about 85 degrees, e.g., 45 degrees, relative to the first and second outer optical surfaces 138, 139 of the transparent body 110. FIG. 3C shows a single ray 160 passing through the first outer optical surface 138 of the transparent body 110, then into the sample prism chamber 118 and then through the transparent partition wall 150 and into the reference prism chamber 120 and subsequently out of the second optical surface 139 of the transparent body 110. In a balance condition, the refractive indices of fluids in the sample and reference prism chambers 118, 120 are the same and the ray 160 passes through the chambers 118, 120 without a change in its inclination angle. A second ray 162 corresponds to a condition in which the refractive index of a sample fluid in the sample prism chamber 118 differs from the refractive index of a reference fluid in the reference prism chamber 120, leading to a net deflection of the incident ray.

In practice, the conventional flow cell 10 in FIG. 2 may be rotated by a small angle about the longitudinal axis 30 of the transparent body 12 in order to minimize light that could be specularly reflected from the flow cell 10 onto a light-sensitive portion of a detector. When this is carried out with the flow cell 100 of FIGS. 3A and 3B having the echelle grating, the slight rotation produces a shadowing effect by each step 'tread 142,' leading to some reduction in overall detected signal.

Figure 4:
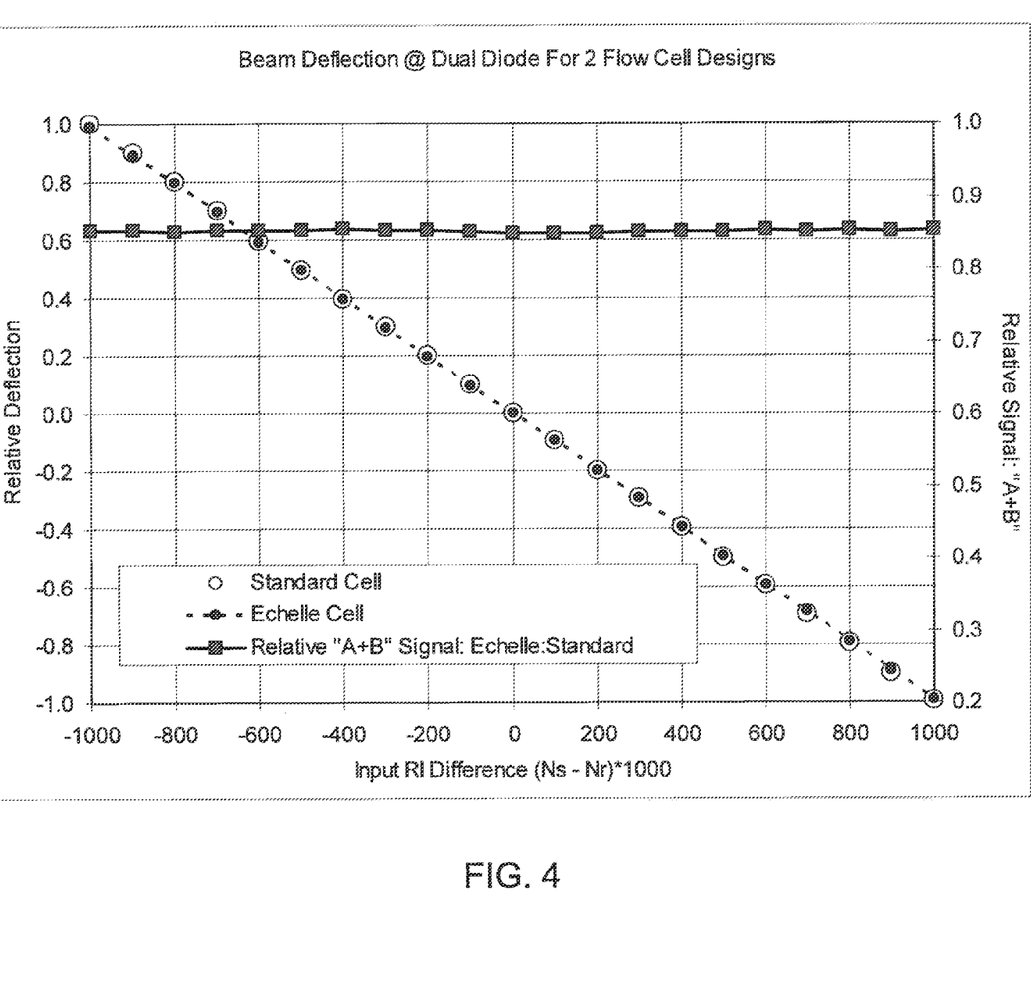
FIG. 4 compares calculated RI response for a prior art flow cell and one having an echelle flow cell for differential refractive index detection.

FIG. 4 depicts a comparison of a calculated response (calculated utilizing OptiCAD® Ray Trace Software, available from OptiCAD Corporation of Santa Fe, New Mex.) for both flow cell geometries (i.e., comparing conventional flow cell 10 and flow cell 100) as a function of RI difference. When there is no difference in RI between the sample and reference prism chambers, there is no change in the angular deflection of the input beam after passing through the flow cell the two rays (depicted in FIG. 2 with respect to the conventional flow cell and in FIG. 3C for the 'echelle' flow cell) coalesce. With changing RI, the beam is deflected to an extent controlled by the prism angle and known opto-mechanical design factors; the 'echelle' deflection (i.e., the deflection attributable to the echelle grating) is only 0.8% less than the response in the conventional flow cell and is linear over the tested range of RI difference.

Also shown in FIG. 4, with reference to the right-hand side ordinate, is the relative signal level (corresponding to a total number of ray 'spots' falling on a detector (two photodiodes)) for the two flow cell geometries. The graph depicts a horizontal line at a relative signal level of 0.85, meaning the echelle flow cell 100 transmits about 15% less energy than the conventional flow cell 10. The difference is ascribable to the shadowing effect. Each flow cell type is rotated by a small angle (e.g., about 0.5° to about 5°, e.g., 2.5°), in a direction which, in the case of the echelle cell 100, reveals part of the tread 142 (FIG. 3B) to the incoming light. The specific mechanical parameters of the echelle cell together with the cell rotation angle fully account for the 15% reduction in energy which should have very little effect on overall analytical sensitivity.

The transparent body 110 of the flow cell 100 should be made of materials that are light transmissive over the range of wavelengths emanating from the lightsource. Non light transmissive portions of the flow cell 100, which could include end caps 132 may be made of the same material as the body 110 for ease of manufacture. For example, the flow cell 100 can be formed according to a known process in which discrete substrates of silica are individually formed, e.g., via machining, laser or chemical etching, and then stacked to achieve the desired geometry. The stacked substrates are subjected to high temperature fusions to bond the substrates and thereby form a unitary structure. This process can include intermediate polishing (e.g., between the fusion bonding of various layers), and adding (drilling) fluid ports, etc. Fused silica is highly transmissive over wavelengths from about 0.02 microns to about 3 microns. Other materials might include borosilicates, certain oxides, fluorides, chalcogenides, etc.

Alternatively, the flow cell 100 can be formed of (e.g., molded from) an optical grade transparent polymer such as polycarbonate or cyclo-olefin polymers (COP) (e.g., ZEONEX® developed by ZEON Corporation headquartered in Tokyo, Japan). Such a process provides increased manufacturing yield, as compared to more labor intensive and delicate processes required for handling silica, and at comparably lower overall cost. In some cases, the gratings can be provided with a deposition of an appropriate protective surface layer such as sapphire or other chemically inert materials known in the art to make the chamber resistant to typical LC mobile phases, etc. Techniques such as Atomic Layer Deposition may be employed for such purposes; the coatings so produced are conformal in nature, avoiding potentially unwanted build-up of deposited materials from line-of-sight deposition techniques.

Although a few implementations have been described in detail above, other modifications are possible. For example, the echelle gratings can be extended to other prism angles by adjusting the ratio of the tread:riser dimensions, as can the number of steps and how close these steps come to the hypotenuse. In some cases, the reference prism does not have a grating.

Although an example has been provided in which a transparent body of a flow cell is arranged such that than an optical beam (ray) passes through a sample prism chamber prior to passing through a reference prism chamber, in some cases, the flow cell may instead be arranged such that an optical beam passes through the reference prism chamber prior to passing though the sample prism chamber.

In other cases it may be advantageous to mold a single grating structure and combine it with conventionally machined parts for improving overall thermal control of the detection zone.

While the gratings have been illustrated with sharp-edged corners, in some implementations, the ends of the gratings can be provided with rounded corners.

In some implementations, the exterior surfaces of the flow cell body through which light is transmitted could be anti-reflection coated. The property can be chosen based upon the wavelength range of the light employed for the RI measurement. Accordingly, other implementations are within the scope of the following claims.

What is claimed is:

1. A flow cell for differential refractive index detection, the flow cell comprising:
    a transparent body extending from a first end to a second end along a longitudinal axis, the transparent body defining:
        a sample prism chamber configured to allow fluid flow between the first and second ends of the transparent body along the longitudinal axis; and
        a reference prism chamber configured to receive a reference fluid; wherein the sample and reference prism chambers each comprise a grating comprising a plurality of grooves extending along the longitudinal axis in the direction of fluid flow and the gratings provide the prism chambers with an optical edge length the same as an optical edge length of chambers with triangular cross-sections while also providing the prism chambers with a comparatively smaller cross-sectional area.

2. The flow cell of claim 1, wherein the grating is an echelle grating.

3. The flow cell of claim 1, wherein transparent body includes first and second outer optical surfaces with the sample and reference prism chambers being disposed therebetween, and wherein the gratings are arranged parallel to each other and at an angle relative to the first and second outer optical surfaces.

4. The flow cell of claim 1, wherein the gratings provide the prism chambers with a cross-sectional area that is four (4) times smaller than chambers having triangular cross-sections with the same optical edge lengths as the prism chambers.

5. The flow cell of claim 1, wherein the transparent body is formed, at least in part, of silica.

6. The flow cell of claim 1, further comprising a protective surface layer on surfaces of the transparent body defining the sample and reference chambers, wherein the protective surface layer is resistant to chromatography mobile phase.

7. The flow cell of claim 1, wherein the gratings preserve a frontal area for each prism chamber the same as a frontal area of a prism chamber with the triangular cross-section.

8. The flow of claim 1, wherein the grating provides each prism chamber with a comparatively smaller volume than a prism chamber with the triangular cross-section.

9. The flow cell of claim 1, wherein the transparent body comprises a transparent partition wall separating the sample and reference prism chambers, the partition wall comprising a first smooth surface defining a boundary of the sample prism chamber and a second smooth surface, opposite the first smooth surface, defining a boundary of the reference prism chamber.

10. The flow cell of claim 9, wherein the transparent body includes first and second outer optical surfaces with the sample and reference prism chambers being disposed therebetween, and
    wherein the smooth surfaces of the transparent partition wall are arranged parallel to the gratings and at an angle relative to the first and second outer optical surfaces.

11. The flow cell of claim 1, wherein the transparent body is formed, at least in part, of an optical grade transparent polymer.

12. The flow cell of claim 11, wherein the optical grade transparent polymer is selected from the group consisting of polycarbonate, acrylics, and cyclo-olefin polymers.

13. A flow cell for differential refractive index detection, the flow cell comprising:
    a transparent body extending from a first end to a second end along a longitudinal axis, the transparent body defining:
        a first prism chamber configured to allow fluid flow between the first and second ends of the transparent body along the longitudinal axis; and
        a second prism chamber;
    wherein the first prism chamber comprises a grating comprising a plurality of grooves extending along the longitudinal axis in the direction of fluid flow and wherein the grating provides the first prism chamber with an optical edge length the same as an optical edge length of a chamber with a triangular cross-section whole also providing the first prism chambers with a comparatively smaller cross-sectional area.

14. The flow cell of claim 13, wherein the grating is an echelle grating.

15. The flow cell of claim 13, wherein the grating provides the first prism chamber with a cross-sectional area that is four (4) times smaller than a chamber having a triangular cross-section with the same optical edge length as the first prism chamber.

16. The flow cell of claim 13, wherein the transparent body is formed of silica.

17. The flow cell of claim 13, wherein the grating comprises a protective surface layer.

18. The flow cell of claim 13, wherein the transparent body is formed of an optical grade transparent polymer.

19. The flow cell of claim 18, wherein the optical grade transparent polymer is selected from the group consisting of polycarbonate and cyclo-olefin polymers.

20. The flow cell of claim 13, wherein transparent body includes first and second outer optical surfaces with the first and second prism chambers being disposed therebetween, and
    wherein the grating is arranged at an angle relative to the first and second outer optical surfaces.

21. The flow cell of claim 4, wherein the grating is arranged at an angle of about 5 degrees to about 85 degrees relative to the first and second outer optical surfaces.

22. The flow cell of claim 21, wherein the grating is arranged at an angle of 5 degrees relative to the first and second outer optical surfaces.

23. The flow cell of claim 13, wherein the transparent body comprises a transparent partition wall separating the first and second prism chambers, the partition wall comprising a first smooth surface defining a boundary of the first prism chamber and a second smooth surface, opposite the first smooth surface, defining a boundary of the second prism chamber.

24. The flow cell of claim 23, wherein the transparent body includes first and second outer optical surfaces with the first and second prism chambers being disposed therebetween, and wherein the smooth surfaces of the transparent partition wall are arranged parallel to the grating and at an angle relative to the first and second outer optical surfaces.

25. The flow cell of claim 24, wherein the transparent partition wall is arranged at an angle of about 5 degrees to about 85 degrees relative to the first and second outer optical surfaces.

26. The flow cell of claim 25, wherein the transparent partition wall is arranged at an angle of 45 degrees relative to the first and second outer optical surfaces.

27. A method comprising:
directing an optical beam through a flow cell containing sample and reference prism chamber, conveying a fluid flow through the sample prism chamber;
detecting presence of an analyte in the fluid flow based on a detected deflection of the optical beam, wherein the sample prism chamber includes a grating comprising a plurality of grooves extending parallel to the direction of the fluid flow and wherein the grating provides the sample prism chamber with an optical edge length the same as an optical edge length of a chamber with a triangular cross-section while also providing the sample chamber with a comparatively smaller cross-sectional area.

28. The method of claim 27, comprising detecting deflection of the optical beam with one or more detectors.

29. The method of claim 27, wherein the conveyed fluid flow comprises eluent from a chromatography column.

30. A method comprising:
molding an optical grade transparent polymer to form at least part of a transparent body for a flow cell, the transparent body defining:
a sample prism chamber configured to allow fluid flow through the transparent body and comprising a grating, the grating comprising a plurality of grooves extending parallel to the direction of the fluid flow wherein the grating provides the sample prism chamber with an optical edge length the same as an optical edge length of a chamber with a triangular cross-section while also providing the sample prism chamber with a comparatively smaller cross-sectional area;
a reference prism chamber configured to receive a reference fluid; and
depositing a protective surface layer on surfaces of the transparent body to make the sample and reference chambers resistant to fluids that are to be contained within sample and reference chambers.

* * * * *